(12) United States Patent
Roe et al.

(10) Patent No.: US 7,244,264 B2
(45) Date of Patent: Jul. 17, 2007

(54) DUAL BLADE LANCING TEST STRIP

(75) Inventors: Steven N. Roe, San Mateo, CA (US); Jeffrey N. Roe, San Ramon, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 777 days.

(21) Appl. No.: 10/308,463

(22) Filed: Dec. 3, 2002

(65) Prior Publication Data

US 2004/0106941 A1 Jun. 3, 2004

(51) Int. Cl.
*A61B 17/32* (2006.01)
(52) U.S. Cl. .................................... 606/181
(58) Field of Classification Search .............. 606/181, 606/182, 183, 184, 167, 170, 131, 132, 133
See application file for complete search history.

(56) References Cited

U.S. PATENT DOCUMENTS

| 1,328,459 A | 1/1920 | Smith |
| 2,359,550 A | 10/1944 | Eriksen .................. 128/253 |
| 2,646,799 A | 7/1953 | Jacoby, Jr. ................ 128/314 |
| 2,801,633 A | 8/1957 | Ehrlich .................... 128/314 |
| 3,802,842 A | 4/1974 | Lange et al. ................ 25/253 |
| D234,644 S | 3/1975 | Sugiyama et al. |
| 4,061,468 A | 12/1977 | Lange et al. ................. 23/253 |
| 4,490,465 A | 12/1984 | Limbach et al. .............. 435/14 |
| 4,627,445 A | 12/1986 | Garcia et al. |
| 4,637,403 A | 1/1987 | Garcia et al. |
| 4,787,398 A | 11/1988 | Garcia et al. |
| 4,869,249 A | 9/1989 | Crossman et al. |
| 4,924,879 A | 5/1990 | O'Brien .................... 128/770 |
| 5,100,391 A | 3/1992 | Schutte et al. .............. 606/167 |
| 5,286,362 A | 2/1994 | Hoenes et al. |
| 5,288,636 A | 2/1994 | Pollmann et al. |
| 5,437,999 A | 8/1995 | Diebold |

(Continued)

FOREIGN PATENT DOCUMENTS

DE 102 22 428 12/2002

(Continued)

OTHER PUBLICATIONS

Aoki, Morita, Niwa, Tabei, Quantitative analysis of reversible diffusion-controlled currents of redox soluble species at interdigitated array electrodes under steady-state conditions, Journal of Electroanalytical Chemistry, Dec. 9, 1986.

(Continued)

*Primary Examiner*—Kevin Truong
(74) *Attorney, Agent, or Firm*—Woodard, Emhardt, Moriarty, McNett & Henry LLP

(57) ABSTRACT

An integrated lancing test strip includes a pair of blade members that each have a lancing tip that are configured to lance skin. A pair of spacer members connect the blade members together such that the blade members define an internal capillary. A test strip is positioned along the internal capillary, and the test strip is configured to test analyte levels in the bodily fluid. During use, the lancing tips form one or more incisions in the skin. The fluid from the incisions is drawn via capillary action through the internal capillary and onto the test strip.

38 Claims, 2 Drawing Sheets

U.S. PATENT DOCUMENTS

| | | | |
|---|---|---|---|
| 5,547,702 A | 8/1996 | Gleisner | |
| 5,575,895 A | 11/1996 | Ikeda et al. | |
| 5,607,437 A | 3/1997 | Simon et al. | 606/166 |
| 5,670,031 A | 9/1997 | Hintsche et al. | |
| RE35,803 E | 5/1998 | Lange et al. | 606/182 |
| 5,776,719 A | 7/1998 | Douglas et al. | 435/28 |
| 5,798,031 A | 8/1998 | Charlton et al. | |
| 5,824,491 A | 10/1998 | Priest et al. | 435/28 |
| 5,830,225 A | 11/1998 | Detsch | 606/167 |
| 5,857,983 A | 1/1999 | Douglas et al. | 600/538 |
| 5,869,972 A | 2/1999 | Birch et al. | |
| 5,871,494 A | 2/1999 | Simons et al. | |
| 5,879,311 A | 3/1999 | Duchon et al. | 600/583 |
| 5,931,846 A | 8/1999 | Simon et al. | 606/166 |
| 5,951,492 A | 9/1999 | Douglas et al. | 600/583 |
| 5,951,493 A | 9/1999 | Douglas et al. | 600/583 |
| 5,962,215 A | 10/1999 | Douglas et al. | 435/4 |
| 5,964,718 A | 10/1999 | Duchon et al. | 600/583 |
| 5,971,941 A | 10/1999 | Simons et al. | |
| 5,997,817 A | 12/1999 | Crismore et al. | |
| 6,036,919 A | 3/2000 | Thym et al. | |
| 6,036,924 A | 3/2000 | Simons et al. | |
| 6,048,352 A | 4/2000 | Douglas et al. | 600/181 |
| 6,071,294 A | 6/2000 | Simons et al. | |
| 6,086,545 A | 7/2000 | Roe et al. | 600/570 |
| 6,099,484 A | 8/2000 | Douglas et al. | 600/583 |
| 6,103,033 A | 8/2000 | Say et al. | |
| 6,143,164 A | 11/2000 | Heller et al. | |
| 6,159,424 A | 12/2000 | Kauhaniemi et al. | |
| 6,174,420 B1 | 1/2001 | Hodges et al. | |
| 6,180,062 B1 | 1/2001 | Naka et al. | |
| 6,183,489 B1 | 2/2001 | Douglas et al. | 606/181 |
| 6,258,254 B1 | 7/2001 | Miyamoto et al. | |
| 6,270,637 B1 | 8/2001 | Crismore et al. | |
| 6,287,451 B1 | 9/2001 | Winarta et al. | |
| 6,309,526 B1 | 10/2001 | Fujiwara et al. | |
| 6,315,738 B1 | 11/2001 | Nishikawa et al. | |
| 6,332,871 B1 | 12/2001 | Douglas et al. | 600/583 |
| 6,352,514 B1 | 3/2002 | Douglas et al. | |
| 6,364,890 B1 * | 4/2002 | Lum et al. | 606/181 |
| 6,409,740 B1 | 6/2002 | Kuhr et al. | 606/182 |
| 6,458,258 B2 | 10/2002 | Taniike et al. | |
| 6,561,989 B2 | 5/2003 | Whitson | |
| 6,599,407 B2 | 7/2003 | Taniike et al. | |
| 6,616,616 B2 | 9/2003 | Fritz et al. | |
| 6,676,995 B2 | 1/2004 | Dick et al. | |
| 6,689,411 B2 | 2/2004 | Dick et al. | |
| 6,787,013 B2 | 9/2004 | Chang et al. | |
| 6,800,488 B2 | 10/2004 | Khan et al. | |
| 2002/0002344 A1 | 1/2002 | Douglas et al. | |
| 2002/0004196 A1 | 1/2002 | Whitson | 435/4 |
| 2002/0016006 A1 | 2/2002 | Wendelbo et al. | |
| 2002/0092612 A1 | 7/2002 | Davies et al. | |
| 2002/0103499 A1 | 8/2002 | Perez et al. | |
| 2002/0177763 A1 | 11/2002 | Burns et al. | |
| 2002/0177788 A1 | 11/2002 | Hodges et al. | |
| 2003/0050573 A1 | 3/2003 | Kuhr et al. | |
| 2003/0153939 A1 | 8/2003 | Fritz et al. | |
| 2004/0106941 A1 | 6/2004 | Roe et al. | |
| 2005/0008537 A1 | 1/2005 | Mosoiu et al. | |
| 2005/0013731 A1 | 1/2005 | Burke et al. | |
| 2005/0016844 A1 | 1/2005 | Burke et al. | |
| 2005/0019212 A1 | 1/2005 | Bhullar et al. | |

FOREIGN PATENT DOCUMENTS

| | | |
|---|---|---|
| EP | 0 267 724 | 5/1988 |
| EP | 0 471 986 | 2/1992 |
| EP | 1 260 589 A1 | 11/2002 |
| EP | 1 281 352 A1 | 2/2003 |
| EP | 1 316 367 | 6/2003 |
| EP | 1 324 038 | 7/2003 |
| EP | 1 431 758 | 6/2004 |
| JP | 10 307119 A1 | 11/1998 |
| JP | 11 337514 A1 | 12/1999 |
| WO | WO 93/09710 | 5/1993 |
| WO | WO 93/09723 | 5/1993 |
| WO | WO 97/34140 | 9/1997 |
| WO | WO 98/30904 | 7/1998 |
| WO | WO 00/18294 | 4/2000 |
| WO | WO 00/33063 | 6/2000 |
| WO | WO00/40150 | 7/2000 |
| WO | WO 01/25775 A1 | 4/2001 |
| WO | WO 01/72220 A1 | 10/2001 |
| WO | WO 02/32559 | 4/2002 |
| WO | WO 02/054055 A1 | 7/2002 |
| WO | WO 02/056751 A2 | 7/2002 |
| WO | WO 02/057781 A2 | 7/2002 |
| WO | WO 03/029804 | 4/2003 |
| WO | WO 03/043945 | 5/2003 |
| WO | WO 03/044511 A1 | 5/2003 |
| WO | WO 03/091717 | 11/2003 |
| WO | WO 2004/113901 A1 | 12/2004 |

OTHER PUBLICATIONS

Cosofret, Erdosy, Johnson, Buck, Ash, Neuman, Microfabricated Sensor Arrays Sensitive to pH and K+ for Ionic Distribution Measurements in the Beating Heart, Analytical Chemistry, May 15, 1995.

Fietzek, Hesser, Turk, Voges, Verarbeitung von Dispersionshaftklebstoffen, Adhasion, Dec. 1993.

Horiuchi, Niwa, Morita, Tabei, Limiting Current Enhancement by Self-Induced Redox Cycling on a Micro-Macro Twin Electrode, Journal of the Electrochemical Society, Dec. 1991.

Koichi Aoki, Theory of the steady-state current of a redox couple at interdigitated array electrodes of which pairs are insulated electrically by steps, Journal of Electroanalytical Chemistry, Oct. 10, 1989.

Niwa, Morita, Tabei, Fabrication and characteristics of vertically separated interdigitated array electrodes, Journal of Electroanalytical Chemistry, Aug. 10, 1989.

Tender, Worley, Fan, Lopez, Electrochemical Patterning of Self-Assembled Monolayers onto Microscopic Arrays of Gold Electrodes Fabricated by Laser Ablation, Langmuir, 1996.

* cited by examiner

DUAL BLADE LANCING TEST STRIP

BACKGROUND OF THE INVENTION

The present invention generally relates to bodily fluid sampling devices and more specifically, but not exclusively, concerns an integrated lancing test strip.

General Fluid Testing

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

General Test Steps

The testing of bodily fluids basically involves the steps of obtaining the fluid sample, transferring the sample to a test device, conducting a test on the fluid sample, and displaying the results. These steps are generally performed by a plurality of separate instruments or devices.

Acquiring—Vascular

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

Acquiring—Incising

The other common technique for collecting a bodily fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the bodily fluid from the incision site.

Various methods and systems for incising the skin are known in the art. Exemplary lancing devices are shown, for example, in U.S. Pat. No. Re 35,803, issued to Lange, et al. on May 19, 1998.; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek Softclix lancet.

Expressing

Patients are frequently advised to urge fluid to the incision site, such as by applying pressure to the area surrounding the incision to milk or pump the fluid from the incision. Mechanical devices are also known to facilitate the expression of bodily fluid from an incision. Such devices are shown, for example, in U.S. Pat. No. 5,879,311, issued to Duchon et al. on Feb. 16, 1999, U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of bodily fluid from an incision is the Amira AtLast blood glucose system.

Sampling

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; U.S. Pat. No. 6,099,484, issued to Douglas et al. on Aug. 8, 2000; and U.S. Pat. No. 6,332,871, issued to Douglas et al. on Dec. 25, 2001. Examples of commercial sampling devices include the Roche Compact, Amira AtLast, Glucometer Elite and Therasense FreeStyle test strips.

Testing General

The bodily fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

Blood Glucose

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing bodily fluids for properties on constituents.

Testing Difficulties

Performing the above-discussed steps can be difficult for patients, especially for patients with limited hand dexterity, such as the elderly. In a typical procedure, the patient first creates an incision in the skin by lancing the skin with a lancet. In order to ensure that a sufficient number of capillaries are cut for supplying an adequate bodily fluid sample, the incision has to usually be deep, which can be rather painful for the patient. Often, the incision cite still does not provide an adequate amount bodily fluid for the sample, and the patient then must resort to expressing the fluid for the cite. If during expression of the fluid the patient is not careful, smearing of the fluid may occur, which may result in rendering the sample useless. Once a sufficient amount of fluid collects as a droplet on the skin, the patient has to position a test strip over the cite such that the test strip contacts and absorbs a sufficient amount of the droplet for testing. Usually the droplet of fluid is quite small, and patients, especially ones with hand motor control problems, may experience great difficulty in positioning the test strip so as to collect a sample from the droplet. As should be appreciated, patients can become frustrated by this procedure, and consequently, they may perform the test less often or may even quit testing altogether.

Thus, needs remain for further contributions in this area of technology.

SUMMARY OF THE INVENTION

One form of the present invention generally concerns an integrated lancing test strip device for collecting and analyzing bodily fluid from one or more incisions in the skin. The device includes at least a pair of blade members that define an internal capillary. The blade members have a pair of lancing tips configured to lance the incisions in the skin and positioned to draw bodily fluid from the incisions into the internal capillary via capillary action. Test media is positioned along the internal capillary to analyze the bodily fluid.

Another form concerns an integrated bodily fluid sampling device. The device includes a first blade member that has a first lancing tip configured to lance the skin and a second blade member that has a second lancing tip configured to lance the skin. A pair of spacer members attach the first blade member to the second blade member. The blade members and the spacer members define a cavity to collect bodily fluid. A means for testing the bodily fluid is positioned along the cavity.

A further form concerns a method that includes providing a lancing device. The lancing device includes a pair of blade members that define an internal capillary and a test strip positioned along the internal capillary. One or more incisions are lanced in skin with the blade members. Bodily fluid from the incisions are drawn onto the test strip via capillary action through the internal capillary.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
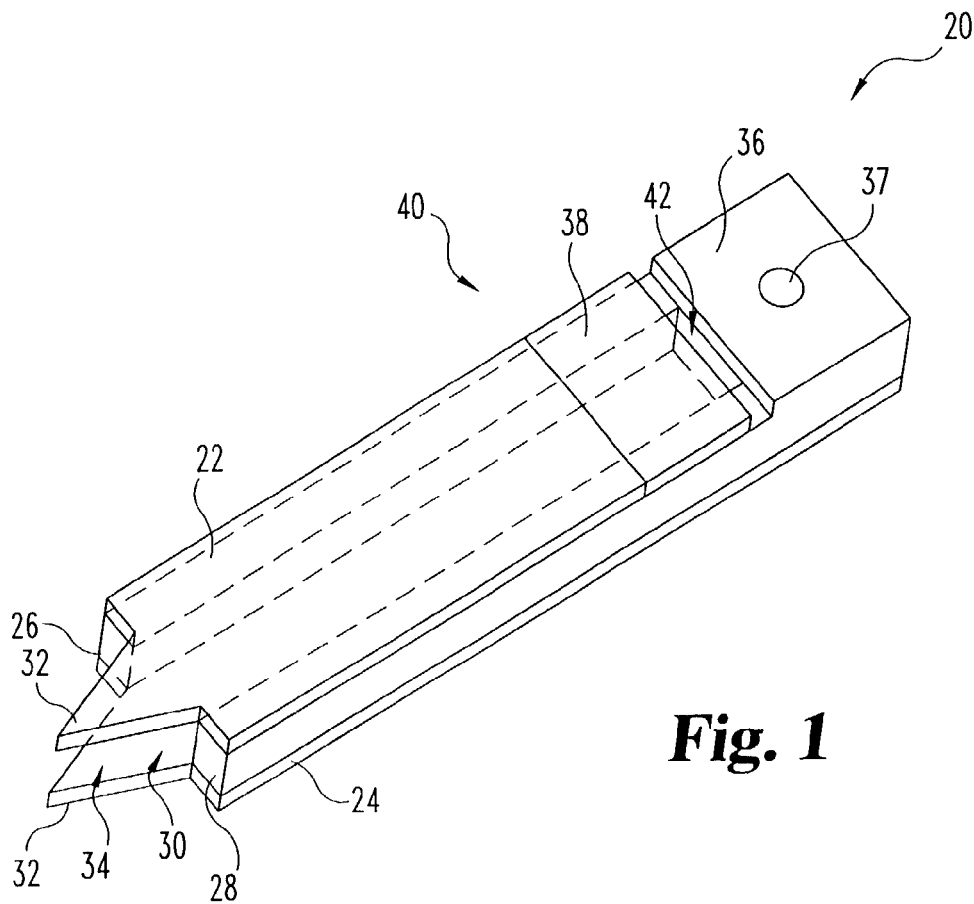
FIG. 1 is a perspective view of an integrated lancet device according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention generally concerns an integrated skin lancing device that reduces the pain as well as the number of steps involved in forming, collecting and testing a bodily fluid sample from an incision. The device includes a pair of generally flat blade members with each having a cutting tip configured to cut an incision into the skin. In one embodiment, the cutting tips extend in generally parallel relationship to one another, and in another embodiment, the tips are angled to contact one another in order to improve their overall strength. In comparison to single blade designs, the two blades of the present invention can cut into the skin at a shallower depth, while still ensuring a sufficient number of capillaries are cut so as to create an adequate fluid supply. By cutting an incision with a shallower depth, less pain may be experienced during lancing. Moreover, the blades can be positioned sufficiently close together such that an incision created by each blade is only sensed by the patient as a single incision. The two blade members are joined together through a pair of spacer or adhesive beads that define an internal capillary channel between the blade members. In one form of the present invention, the capillary channel is empty such that fluid is drawn via capillary action through the capillary channel. In another form of the present invention, the capillary channel is filled with a wicking material that transports the bodily fluid sample. Along the capillary channel, the lancet includes a test strip that is configured to test analyte levels in the sample.

During use, the lancet device is extended to lance a pair of incisions in the skin. After the incisions are formed, the cutting tips are withdrawn from the incisions to a position proximal the incisions. As the bodily fluid from the incisions collects on the skin, the fluid is drawn into the gap between the two blade tips and into the internal capillary via capillary action. Next, the blood travels through the internal capillary and is deposited on the test strip for testing. As should be appreciated, the integrated, dual blade design of the present invention reduces the pain involved and the number of steps associated with testing.

Figure 2:
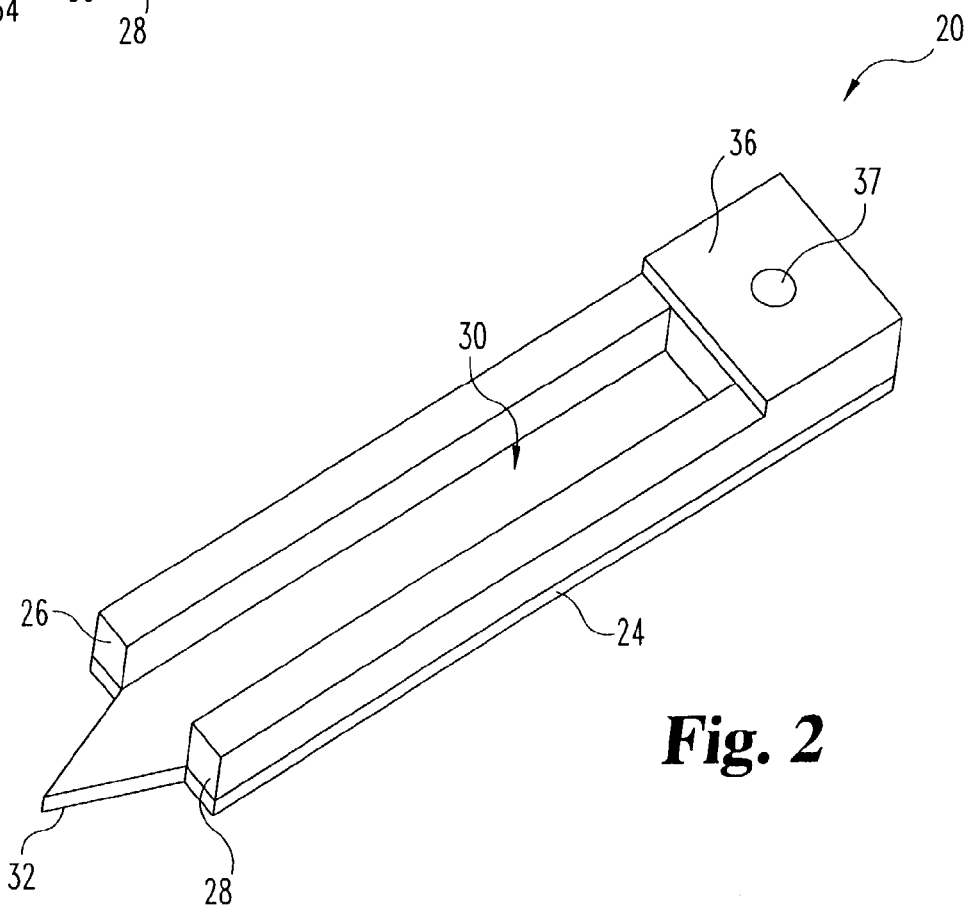
FIG. 2 is a perspective view of the FIG. 1 lancet with the one blade element removed.
Figure 3:
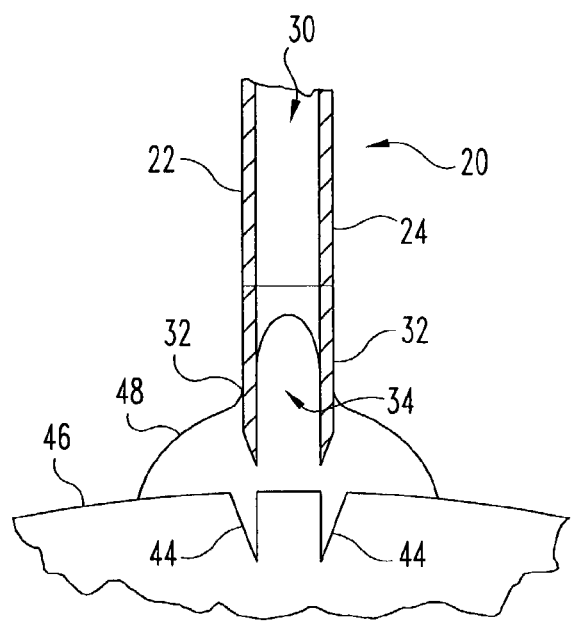
FIG. 3 is a side view of the FIG. 1 lancet drawing fluid from an incision.

A dual blade, integrated lancing test strip or device 20 according to one embodiment of the present invention is illustrated in FIGS. 1-3. As shown in FIG. 1, the lancing device 20 includes first 22 and second 24 blade members that extend in a parallel relationship. In the illustrated embodiment, blade members 22 and 24 have a generally flat shape such that device 20 is in the form of a flat lancet. By being generally flat, blade members 22 and 24 can be easily formed from sheets of material, such as metal, and these sheets can be sandwiched together to form mass quantities of the lancing devices 20 at the same time. Moreover, the flat design allows multiple lancing devices 20 to be connected together so as to be used in a cartridge, such as the drum in an ACCU-CHEK COMPACT™ brand meter (Roche Diagnostics Corp., Indianapolis, Ind.). The lancing device 20 can also be a stand-alone lancet that is dispensed and used individually. In one embodiment, blade members 22 and 24 are made of metal, in particular stainless steel, but it should be appreciated that blade members 22 and 24 can be made of other materials, such as plastic and/or ceramics.

Spacer members 26 and 28 join the first 22 and second 24 blade members together so as to define an internal capillary 30. Spacer members 26 and 28 in one embodiment are beads of adhesive, and in another embodiment are strips of adhesive tape. As should be appreciated, spacer members 26 and 28 can be made of other materials. The internal capillary 30 formed between the blade members 22, 24 is sized to draw fluid via capillary action. For instance, blade members 22 and 24 in one form of the present invention are spaced apart from one another between two-thousandths of an inch (0.002") and ten-thousandths of an inch (0.010") to form the internal capillary 30 of that size. In another form, blade members 22 and 24 are preferably spaced apart between about two-thousandths of an inch (0.002") to three-thousandths of an inch (0.003") so as to improve the flow rate in the internal capillary 30.

Each blade 22, 24 has a lancing tip 32 at one end that define a capillary gap 34, which opens into one end of the internal capillary 30. As depicted in FIG. 2, the other end of the internal capillary 30 is enclosed by a vent block 36. The vent block 36 in one embodiment is made of plastic, but it should be appreciated that vent block 36 can be made from other materials. By way of nonlimiting examples, the vent block 36 can be made from metal, plastic, an adhesive bead, and/or adhesive tape, to name a few.

The lancing tips 32 are shaped to cut an incision in the skin. In the embodiment illustrated in FIG. 1, the lancing tips 32 of the first 22 and second 24 blade members extend in a parallel relationship with respect to one another and have a general triangular shape. The lancing tips 32 in other embodiments, however, can have a different shape. As will be discussed in further detail below, by extending parallel to one another, the tips 32 are able to cut a pair of incisions in the skin. It should be understood that device 20 in other embodiments can incorporated more than two lancing tips 32. By having two (or more) lancing tips 32, a more shallow penetration depth may be used to collect the same amount of fluid, thereby reducing the associated pain with lancing.

It has also been discovered that the distance between nerve endings varies depending on the location on the body. For instance, nerve endings are highly concentrated in the fingertips and are less concentrated along the forearm. The lancing tips 32 in one embodiment are spaced apart a small distance such that the nerves endings in the patient are unable to differentiate between the two incisions formed by the lancing tips 32 so that the patient only experiences the sensation of a single incision. In other embodiments, the spacing between the lancing tips 32 can be sized depending on the location where the incision is desired to be formed. In one particular embodiment, the tips 32 are spaced apart between two-thousandths of an inch (0.002") to three-thousandths of an inch (0.003").

Referring to FIG. 1, the vent block 36 defines a registration opening 37, and a test strip or media 38 is positioned along the internal capillary 30 in order to receive fluid drawn by the internal capillary 30. The test strip 38 is operable to test analyte levels in bodily fluid. The test strip 38 can analyze fluid through such means as optical (e.g., reflectance, absorption, fluorescence, Raman, etc.), electrochemical, and magnetic analysis, to name a few. In one embodiment, the test strip 38 analyzes the fluid optically. Among its many functions, the registration opening 37 is used to align device 20 in a testing system such that the test strip 38 is properly positioned for analysis. As shown, a test strip opening 40 is defined between the vent block 36 and the first blade member 22. The test strip 38 in FIG. 1 is attached to the spacer members 26, 28 in the test strip opening 40. Generally, test strips can be sensitive to environmental factors that exist during sterilization. So as to avoid the need to recalibrate the test strip 38 after sterilization, the test strip 38 in one embodiment is attached after sterilization of the blade members 22, 24. The test strip 38 has a width that is slightly smaller than the width of the test strip opening 40 such that a vent opening 42 is formed between the test strip 38 and the vent block 36. The vent opening 42 allows air to be vented from the internal capillary 30, thereby improving the flow of the bodily fluid within the capillary 30. By integrating the testing as well as the collection of the bodily fluid into the same lancing device 20, less fluid is required in order to provide an adequate sample to the test strip 38.

Referring now to FIG. 3, the lancing device 20 is used to form a pair of incisions 44 in skin 46. After the incisions 44 are formed, the tips 32 are withdrawn from the incisions 44 and positioned proximal to the skin 46 such that bodily fluid 48 is able to freely flow from the incisions 44 and form a drop on the skin 46. The lancing tips 32 can be withdrawn and positioned proximal the drop of fluid 48 either manually by the patient or automatically through the use of a retraction mechanism, such as a spring. As the drop of fluid 48 forms on the skin 46, the fluid 48 is wicked via capillary action into the capillary gap 30. From gap 30, the sample of fluid 48 then travels through the internal capillary 30 and is deposited on the test strip 38. The device 20 remains in position for collecting fluid until a sufficient amount has been collected on the test strip 38. Once a sufficient amount of bodily fluid 48 has been collected, device 20 can be removed from the vicinity of the skin 46.

Figure 4:
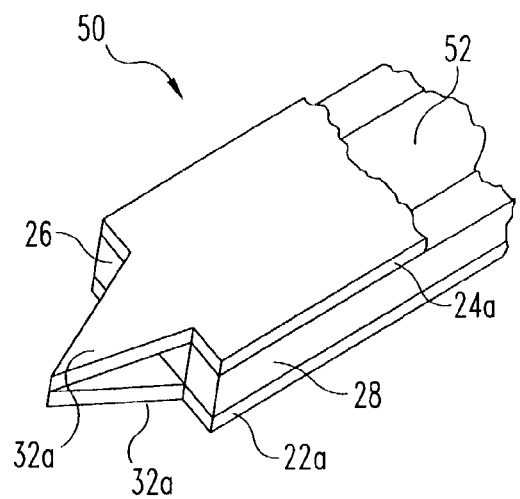
FIG. 4 is a perspective view of an integrated lancet device according to another embodiment of the present invention.

An integrated lancing test strip or device 50, according to another embodiment of the present invention, will now be described with reference to FIGS. 4 and 5. Device 50 has many components similar to the ones described above, with the notable exceptions discussed below. Device 50 includes vent block 36 with registration opening 37, test strip 38, and vent opening 42, which are shown in FIG. 1. As depicted in FIG. 4, device 50 further includes first 22a and second 24a blade members that are attached through the spacer members 26 and 28. As in the previously discussed embodiment, device 50 in FIG. 4 is in the form of a generally flat lancet. The spacer members 26, 28 along with the blade members 22a, 24a define an internal capillary 30a. In the illustrated embodiment, wicking material 52 is received in the internal capillary for drawing fluid to the test strip 38. The wicking material can be selected from various materials including, but not limited to, Pall Accuwick and Whatman 41, which provide a high enough capillary action to wick the fluid onto the test strip.

Similar to the embodiment described above, the blade members 22a and 24a have lancing tips 32a extending therefrom. In comparison to the previous embodiment, lancing tips 32a in the embodiment illustrated in FIGS. 4 and 5 are angled towards one another. As shown in the illustrated embodiment, the outermost ends of the lancing tips 32a contact one another. By angling towards one another, tips 32a are able to support one another, thereby increasing the overall strength of the lancing tips 32a. This construction can allow the blade members 22a, 24a to be formed from thinner material, while still having adequate strength for forming an incision. In another embodiment, tips 32a are angled towards one another, but their outermost ends are slightly spaced apart such that tips 32a do not contact one another. With this embodiment, the lancing tips 32a can support one another by contacting during deflection of the lancing tips 32a. Referring again to the embodiment illustrated in FIG. 5, the tips 32a of device 50 define a capillary gap 34a in which bodily fluid is drawn via capillary action. In the illustrated embodiment, the wicking material 52 does not extend into capillary gap 34. However, it is contemplated that in other embodiments the wicking material 52 fills gap 34a.

Figure 5:
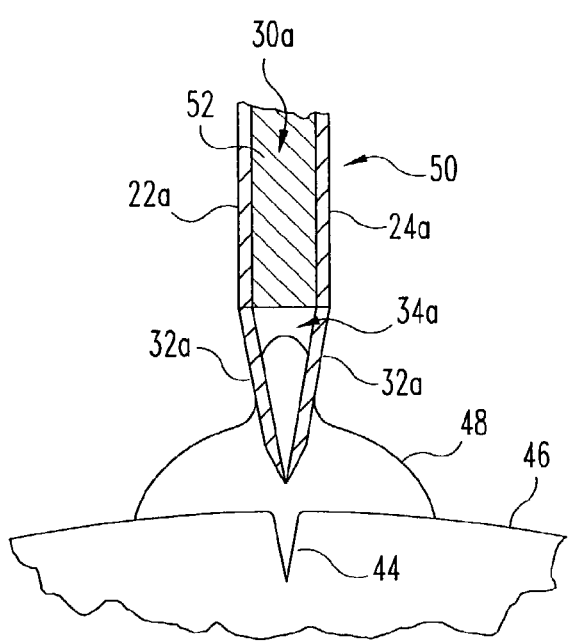
FIG. 5 is a side view of the FIG. 4 lancet drawing fluid from an incision.

As shown in FIG. 5, device 50 samples fluid in a manner very similar to the embodiment described above. However, when tips 32a in device 50 contact each other, only a single incision 44 is formed in the skin. It should be appreciated that when the lancing tips 32a are slightly spaced apart, two incisions 44 can be formed in the skin 46. As in the embodiment before, tips 32a are positioned proximal to the incision 44 after lancing so as to be able to collect bodily fluid 48 from the incision 44. As shown, the bodily fluid 48 is drawn into gap 34a and then into the wicking material 52 in internal capillary 30a. The wicking material 52 deposits the bodily fluid 48 onto the test strip 38.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An integrated lancing test strip device for collecting and analyzing bodily fluid from one or more incisions in skin, comprising:
    at least a pair of blade members defining an internal capillary;
    the blade members having at least a pair of lancing tips that are configured to lance the one or more incisions in the skin and positioned to draw bodily fluid from the one or more incisions into the internal capillary via capillary action; and
    test media positioned along the internal capillary to analyze the bodily fluid.

2. The device of claim 1, wherein the lancing tips are oriented parallel to one another.

3. The device of claim 1, wherein the lancing tips are angled towards one another.

4. The device of claim 3, wherein the lancing tips touch one another.

5. The device of claim 1, further comprising at least a pair of spacer members attached between the blade members.

6. The device of claim 1, further comprising:
    a vent block provided at one end of the capillary opposite the lancing tips; and
    wherein the test media and the vent block define a vent opening for exhausting gas from the internal capillary.

7. The device of claim 6, wherein said vent block defines a registration opening for aligning the device.

8. The device of claim 1, further comprising wicking material received in the internal capillary.

9. The device of claim 1, wherein the test media includes a reagent test strip.

10. The device of claim 1, wherein the lancing tips have a triangular cross-sectional shape.

11. The device of claim 1, wherein the blade members are flat.

12. The device of claim 11, further comprising:
    at least a pair of spacer members attached between the blade members;
    a vent block provided at one end of the capillary opposite the lancing tips, said vent block defining a registration opening for aligning the device, wherein the vent block defines a vent opening for exhausting gas from the internal capillary; and
    wherein the lancing tips have a triangular cross-sectional shape.

13. The device of claim 12, wherein the lancing tips are oriented parallel to one another.

14. The device of claim 12, wherein the lancing tips are angled towards one another.

15. The device of claim 14, further comprising wicking material received in the internal capillary.

16. An integrated bodily fluid sampling device, comprising:
    a first blade member having a first lancing tip configured to lance skin;
    a second blade member having a second lancing tip configured to lance the skin;
    at least a pair of spacer members attaching the first blade member to the second blade member, the blade members and the spacer members defining a cavity to collect bodily fluid; and
    means for testing the bodily fluid positioned along the cavity.

17. The device of claim 16, wherein the means for testing the bodily fluid includes a reagent test strip adapted to indicate analyte levels in the bodily fluid.

18. The device of claim 16, wherein the first and second lancing tips have a generally triangular cross sectional shape.

19. The device of claim 16, wherein the first blade member is flat.

20. The device of claim 19, wherein the second blade member is flat.

21. The device of claim 16, wherein the lancing tips extend parallel to one another.

22. The device of claim 16, wherein the first and second lancing tips angle towards one another.

23. The device of claim 22, wherein the first and second lancing tips contact one another.

24. The device of claim 16, wherein the first and second lancing tips define a capillary gap configured to draw the bodily fluid via capillary action.

25. The device of claim 16, further comprising a vent member enclosing one end of the cavity opposite the first and second lancing tips.

26. The device of claim 25, wherein the means for testing the bodily fluid is positioned along the cavity between the first blade member and the vent member.

27. The device of claim 26, wherein the means for testing the bodily fluid and the vent member define a vent opening for exhausting gas from the cavity.

28. The device of claim 25, wherein the vent member defines a registration opening.

29. The device of claim 16, wherein the cavity includes an internal capillary sized to draw the bodily fluid via capillary action.

30. The device of claim 16, further comprising wicking material received in the cavity.

31. The device of claim 16, wherein the first and second blade members are metallic.

32. The device of claim 16, wherein the spacer members include adhesive beads.

33. An apparatus, comprising:
 a sampling device defining a capillary channel for drawing body fluid, the sampling device including
 at least a pair of spacer members that define the capillary channel;
 a vent member extending between the spacer members;
 a testing portion disposed along the capillary channel for analyzing the body fluid, and
 a strip attached to the spacer members, the strip extending across the capillary channel, the strip being spaced away from the vent member to define a vent opening for venting the capillary channel as the body fluid fills the capillary channel.

34. The apparatus of claim 33, wherein:
 the testing portion includes a test strip; and
 the strip disposed across the capillary channel includes the test strip.

35. The apparatus of claim 34, wherein:
 the vent member includes a vent block; and
 the vent opening is defined between the test strip and the vent block.

36. The apparatus of claim 33, wherein the sampling device includes an integrated lancing test strip that includes a pair of blade members defining the capillary channel.

37. The apparatus of claim 33, wherein the vent opening has a slot shape.

38. The apparatus of claim 33, further comprising means for venting the capillary channel, wherein the means for venting the capillary channel includes the vent opening.

* * * * *